United States Patent [19]

Kröning et al.

[11] Patent Number: 4,640,131
[45] Date of Patent: Feb. 3, 1987

[54] METHOD AND APPARATUS FOR THE ULTRASONIC TESTING OF BOLTS WITH A WALL THICKNESS DISCONTINUITY

[75] Inventors: Michael Kröning, Röttenbach; Georg Hölzler, Möhrendorf; Roland Heumüller, Erlangen, all of Fed. Rep. of Germany

[73] Assignee: Kraftwerk Union Aktiengesellschaft, Mülheim, Fed. Rep. of Germany

[21] Appl. No.: 722,298

[22] Filed: Apr. 11, 1985

[30] Foreign Application Priority Data

Apr. 16, 1984 [DE] Fed. Rep. of Germany ....... 3414362

[51] Int. Cl.$^4$ ............................................ G01N 29/04
[52] U.S. Cl. ...................................... 73/600; 73/628; 73/629; 73/637; 73/644
[58] Field of Search .................. 73/600, 628, 629, 637, 73/639, 641, 644

[56] References Cited

U.S. PATENT DOCUMENTS

| 4,435,984 | 3/1984 | Gruber | 73/628 |
| 4,522,064 | 6/1985 | McMillan | 73/600 |

Primary Examiner—Howard A. Birmiel
Attorney, Agent, or Firm—Herbert L. Lerner; Laurence A. Greenberg

[57] ABSTRACT

A method for the ultrasonic testing of bolts for incipient cracks emanating from a wall thickness discontinuity between thinner and thicker parts of the bolt, which includes placing an ultrasound transmitter and receiver in the form of a piezo-electric transducer on the periphery of the thicker part of the bolt with the discontinuity located in the near-field region, radiating longitudinal waves at an angle of 55° to 70° and transversal waves at an angle of 25° to 35° from the transducer in direction toward the discontinuity, and comparing the intensity of reflected transversal and longitudinal waves with an echo characteristic obtained from a test body corresponding to the bolt to be tested, having slots formed therein simulating incipient cracks of different depths, and an apparatus for carrying out the method.

3 Claims, 4 Drawing Figures

METHOD AND APPARATUS FOR THE ULTRASONIC TESTING OF BOLTS WITH A WALL THICKNESS DISCONTINUITY

The invention relates to a method for the ultrasonic testing of bolts for incipient cracks starting from a wall thickness discontinuity, using a transmitter and a receiver for ultrasonic waves, as well as an apparatus for carrying out the method. Such incipient cracks could heretofore only be detected if the ultrasonic test was made from the thinner part of the bolt determined by the wall thickness discontinuity, because otherwise the large ultrasound echoes of the wall thickness discontinuity shielded and falsified the relatively small echo signals of incipient cracks. However, particularly in nuclear plants, tests in the radiation-subjected region can be made only from the thicker side of the bolt, such as because of the use of remote control.

It is accordingly an object of the invention to provide a method and apparatus for the ultrasonic testing of bolts with a wall thickness discontinuity, which overcomes the hereinafore-mentioned disadvantages of the heretofore-known methods and devices of this general type, and to detect incipient cracks in bolts with a wall thickness discontinuity from the thicker side of the bolt.

With the foregoing and other objects in view there is provided, in accordance with the invention, a method for the ultrasonic testing of bolts for incipient cracks emanating from a wall thickness discontinuity between thinner and thicker parts of the bolt, which comprises placing an ultrasound transmitter and receiver in the form of a piezo-electric transducer on the periphery of the thicker part of the bolt with the discontinuity located in the near-field region of the transmitter-transducer, radiating ultrasound longitudinal waves at an angle of 55° to 70° and transversal waves at an angle of 25° to 35° from the transducer into the bolt in direction toward the discontinuity, and comparing the intensity of reflected transversal and longitudinal waves with an echo characteristic obtained from a test body corresponding to the bolt to be tested, having slots formed therein simulating incipient cracks of different depths.

In accordance with another mode of the invention, there is provided a method for the ultrasonic testing of bolts for incipient cracks emanating from a wall thickness discontinuity between thinner and thicker parts of the bolt, which comprises placing a transmitter and a receiver of a tandem ultrasound test head one behind the other in lengthwise or longitudinal direction of the bolt on the periphery of the thicker part of the bolt with the discontinuity in the near-field region of the transmitter, radiating ultrasound transversal waves at an angle of 40° to 70° from the transmitter into the bolt in direction toward the discontinuity, and comparing the intensity of a transversal wave reflected to the receiver with an echo characteristic obtained from a test body corresponding to the bolt to be tested, having slots formed therein simulating incipient cracks of different depths.

Both methods according to the invention have proven themselves very well, so that they can be considered practically equivalent as to sensitivity and accuracy. Furthermore, incipient cracks with depths which are smaller than the height of the wall thickness discontinuity, were readily detectable with these methods.

In order to carry out both methods according to the invention, there is provided an apparatus for the ultrasonic testing of bolts for incipient cracks emanating from a wall thickness discontinuity between thinner and thicker parts of the bolt, comprising a plurality of ultrasound transmitting and receiving test heads combined to form a ring, the ring having an opening formed therein enclosing the thicker part of the bolt for radiating waves from the test heads in a direction toward the discontinuity, means disposed on the ring for centering the bolt and for maintaining the test heads at a distance from the surface of the bolt which is greater than twice the wave length, a selector switch connected to the test heads, and an ultrasonic testing apparatus connected to the selector switch.

Other features which are considered as characteristic for the invention are set forth in the appended claims.

Although the invention is illustrated and described herein as embodied in a method and apparatus for the ultrasonic testing of bolts with a wall thickness discontinuity, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which.

Figure 1:
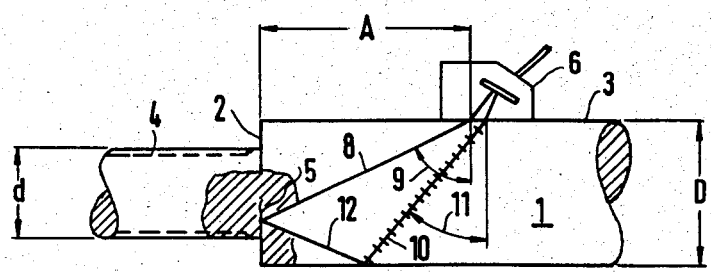
FIGS. 1 and 2 are fragmentary, diagrammatic, cross-sectional views which are partly broken away, of a bolt showing the principles of the new methods for ultrasonic testing of a bolt with a wall thickness discontinuity.

Referring now to the figures of the drawings in detail and first particularly to FIG. 1 thereof, it is seen that a rotation-symmetrical bolt 1 to be tested has a wall thickness discontinuity 2 at the transition from its thicker part 3 to its thinner part 4. The bolt may be a cylindrical guide or holding pin with a diameter D of 22 mm, for example. The thinner part 4 is a threaded post which has a diameter d of 15 mm with an M15 thread.

The wall thickness discontinuity 2 with its right-angle step is particularly endangered by incipient cracks, such as are shown as faults 5. These incipient cracks are to be detected from the thicker side 3, with the method according to the invention. To this end, an ultrasonic test head 6 which works as the transmitter and the receiver, is applied in accordance with FIG. 1.

The ultrasonic test head 6 is mounted tightly on or closely to the periphery of the thicker part 3 of the bolt 1 with a base fitting the surface of the bolt 1. The distance A from the test head 6 to the wall thickness discontinuity 2 is chosen as 21.5 mm, for instance, which is so large that the wall thickness discontinuity lies in the short range or near-field region of the test head 6. A longitudinal-wave main beam 8 is therefore used, which is radiated at a frequency of 4 MHz and an angle 9 of about 65° to the normal or vertical, on the periphery of the bolt 1. However, a transversal-wave main beam 10 entering the bolt 1 at the same time, is radiated at an angle 11 of about 30°. The beam 10 is aimed at the opposite side of the bolt 1, so that a longitudinal beam 12 is generated through wave conversion, which detects the incipient crack 5.

The longitudinal-wave main beam 8 reflected at the incipient crack 5 leads to a transversal-wave echo corresponding to the radiated transversal-wave main beam 10. In the reverse direction, the transversal-wave main beam 10 leads to a signal which is reflected by the incipient crack 5 as the longitudinal-wave beam 8. The intensity of the signals is compared with an echo characteristic 13 shown in FIG. 3. The echo level E is shown in dB on the ordinate 14, and the depth T of the incipient crack is shown in millimeters on the abscissa 15. The echo characteristic 13 reaches a maximum value for T=d, i.e., for the complete separation of the threaded post 4, as the saturation curve.

Figure 2:
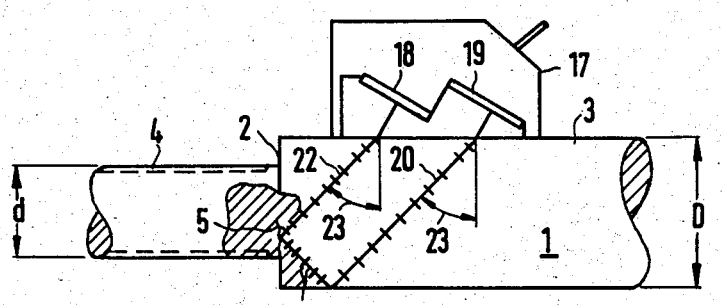
Figure 3:
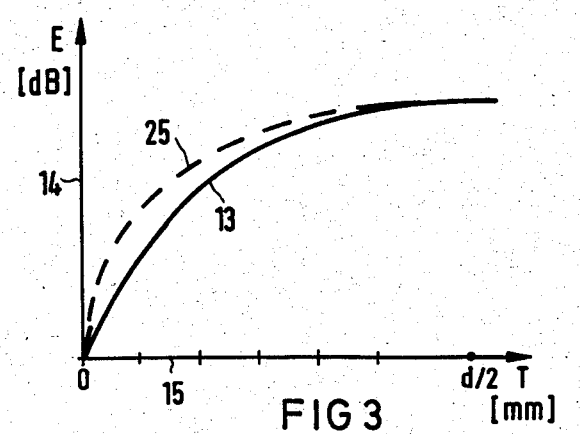
FIG. 3 is a graph of the echo characteristic used for this purpose.

In the embodiment according to FIG. 2, the ultrasonic measurement is carried out with a tandem test head 17, in which a transmitter 18 and a receiver 19 for transversal waves are disposed one behind the other in the longitudinal direction of the bolt 1. The transversal waves indicated by beam sections 20, 21 and 22 are insonified at an angle 23° of 45° relative to the vertical or normal to the bolt surface. The echo characteristic which serves for determining the echo intensity as a measure of incipient cracks, is shown in FIG. 3 by a broken line curve 25, which again approaches a saturation limit for T=d.

Figure 4:
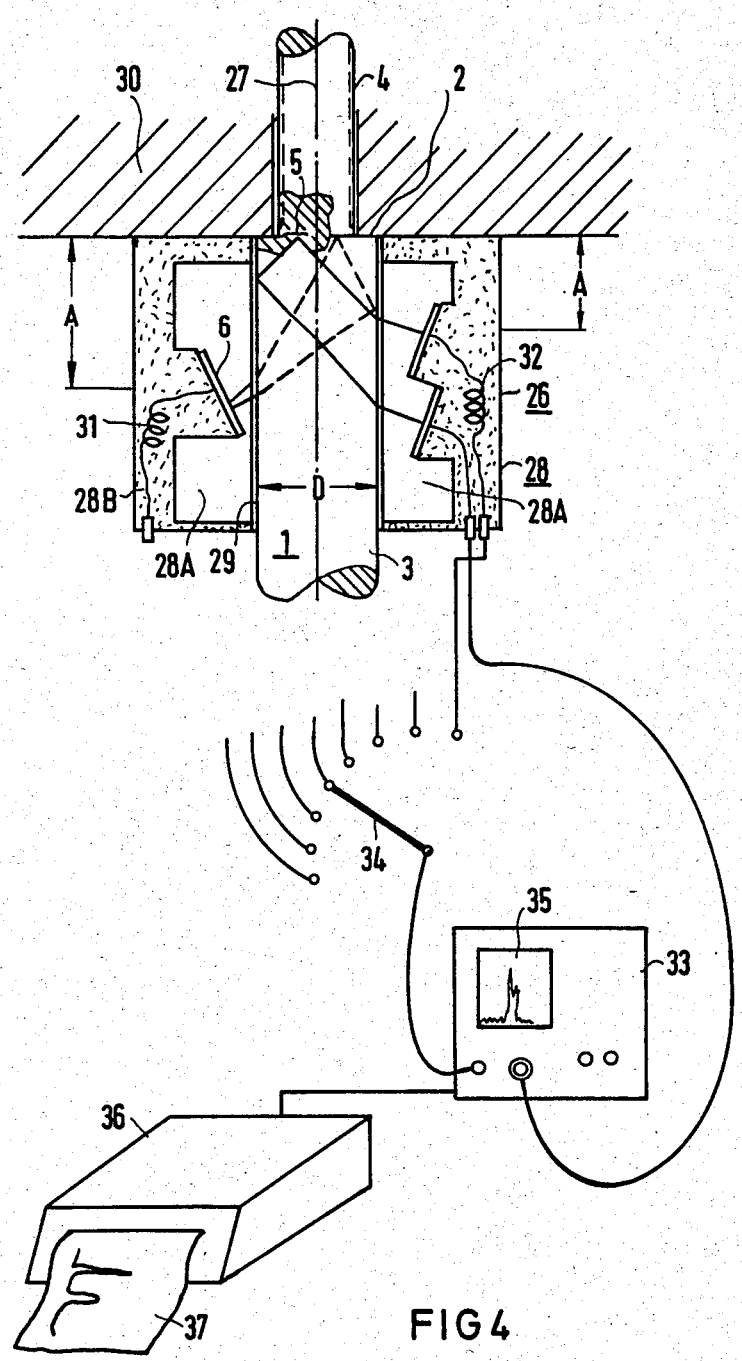
FIG. 4 is a diagrammatic, partly cross-sectional and broken away and partly perspective view of two devices for carrying out the methods according to the invention, being indicated on different sides of the figure.

In the apparatus 26 shown in FIG. 4, two possible modes of performing the methods according to the invention with a disposition of the test heads in a ring configuration 28 are shown on two sides of the dot-dash center line 27 of the bolt 1. The ring configuration 28 includes a plastic ring 28A, preferably formed of plexiglass, with an opening 29 which fits the diameter D of the bolt 1 and at the same time effects a centering of the ring 28 on the bolt 1. A casting compound 28B with damping properties is disposed on the plastic ring 28A. The desired positioning of the ring configuration 28 in the longitudinal or lengthwise direction of the bolt 1, is achieved by placing the ring 28 on a plate 30, in which the threaded post part 4 is placed.

Eight vibrators are uniformly distributed about the rim of the opening 29 in the casting compound 28B. The vibrators are constructed either as a single-vibrator test head 6 according to FIG. 1, or as a tandem test head 17 according to FIG. 2.

The test heads 6, 17 are connected to a selector switch 34 through coils 31 and 32 for electronic matching to an ultrasonic apparatus 33. The switch 34 connects one of the test heads 6 or 17 to the ultrasonic apparatus 33. Echo signals picked up by the respective active test head can be seen on the picture screen 35 of the ultrasonic apparatus 33. However, the echo signals can also be read out by means of a recorder 36 as is shown on a sheet 37 of the recorder. A comparison with the echo characteristic shown in FIG. 3 is then possible again.

In this embodiment, the distance from the test heads 6, 17 to the surface of the bolt, which varies due to the play between the bolt 1 and the opening 29 is larger (with sufficient constancy) than twice the wavelength of 0.8 mm, for instance. For this purpose, wedges or similar clamping devices can also be provided for centering, so as to prevent falsifications of the measurement signal by lateral motion of the ring 28.

The foregoing is a description corresponding in substance to German application No. P 34 14 362.9, filed Apr. 16, 1984, the International priority of which is being claimed for the instant application, and which is hereby made part of this application. Any material discrepancies between the foregoing specification and the aforementioned corresponding German application are to be resolved in favor of the latter.

We claim:

1. Method for the ultrasonic testing of bolts for incipient cracks emanating from a wall thickness discontinuity between thinner and thicker parts of the bolt, which comprises placing an ultrasound transmitter and receiver in the form of a piezoelectric transducer on the periphery of the thicker part of the bolt with the discontinuity located in the near-field region, radiating longitudinal waves at an angle of 55° to 70° and transversal waves at an angle of 25° to 35° from the transducer in direction toward the discontinuity, and comparing the intensity of reflected transversal and longitudinal waves with an echo characteristic obtained from a test body corresponding to the bolt to be tested, having slots formed therein simulating incipient cracks of different depths.

2. Method for the ultrasonic testing of bolts for incipient cracks emanating from a wall thickness discontinuity between thinner and thicker parts of the bolt, which comprises placing a transmitter and a receiver of a tandem ultrasound test head one behind the other in lengthwise direction of the bolt on the periphery of the thicker part of the bolt with the discontinuity in the near-field region of the transmitter, radiating transversal waves at an angle of 40° to 70° from the transmitter in direction toward the discontinuity, and comparing the intensity of a transversal wave reflected to the receiver with an echo characteristic obtained from a test body corresponding to the bolt to be tested, having slots formed therein simulating incipient cracks of different depths.

3. Apparatus for the ultrasonic testing of bolts for incipient cracks emanating from a wall thickness discontinuity between thinner and thicker parts of the bolt, comprising a plurality of ultrasound transmitting and receiving test heads combined to form a ring, said ring having an opening formed therein enclosing the thicker part of the bolt for radiating waves from the test heads in direction toward the discontinuity, means disposed on said ring for centering the bolt and for maintaining the test heads at a distance from the surface of the bolt which is greater than twice the wave length, a selector switch connected to the test heads for individually addressing the test heads, and an ultrasonic testing apparatus connected to said selector switch.

* * * * *